United States Patent [19]

Wiest et al.

[11] Patent Number: 5,044,203

[45] Date of Patent: Sep. 3, 1991

[54] PRESSURE MEASUREMENT DEVICE FOR FLUIDS FLOWING IN LINES

[75] Inventors: Peter P. Wiest, Hessenallee 8, D-1000 Berlin 19; Hubert G. Fuchs, Berlin, both of Fed. Rep. of Germany

[73] Assignee: Peter P. Wiest, Berlin, Fed. Rep. of Germany

[21] Appl. No.: 530,601

[22] Filed: May 30, 1990

[30] Foreign Application Priority Data

May 31, 1989 [DE] Fed. Rep. of Germany ....... 3918142

[51] Int. Cl.⁵ .......................... G01L 7/08; G01L 9/00
[52] U.S. Cl. ................................. 73/730; 73/719 A
[58] Field of Search ............ 73/730, 119 A, 729, 73/731

[56] References Cited

U.S. PATENT DOCUMENTS 2,420,148  5/1947  Ostergren ............................. 73/731
4,702,675  10/1987  Aldrovandi et al. ................ 73/730

Primary Examiner—Donald O. Woodiel
Attorney, Agent, or Firm—McGlew & Tuttle

[57] ABSTRACT

The invention relates to a pressure measurement device (1) for fluids flowing in lines (5, 6), particularly for the flexible tubing lines of pressure-controlled roller pumps (22) for use in arthroscopy and urethroscopy. A membrane (8,8') is provided such that it is impacted on the inside by the fluid. A first pressure sensor (12) is connected to the outside of the membrane for measurement of fluid pressure. The first pressure sensor is connected to an evaluating electronic unit.

A second pressure sensor (13) is connected to the evaluating electronic unit and is assigned to the outer side of membrane (8,8'), so that it is possible to effect a pressure monitoring based on the second pressure measurement, e.g., in the form of a measurement of pressure difference.

11 Claims, 3 Drawing Sheets

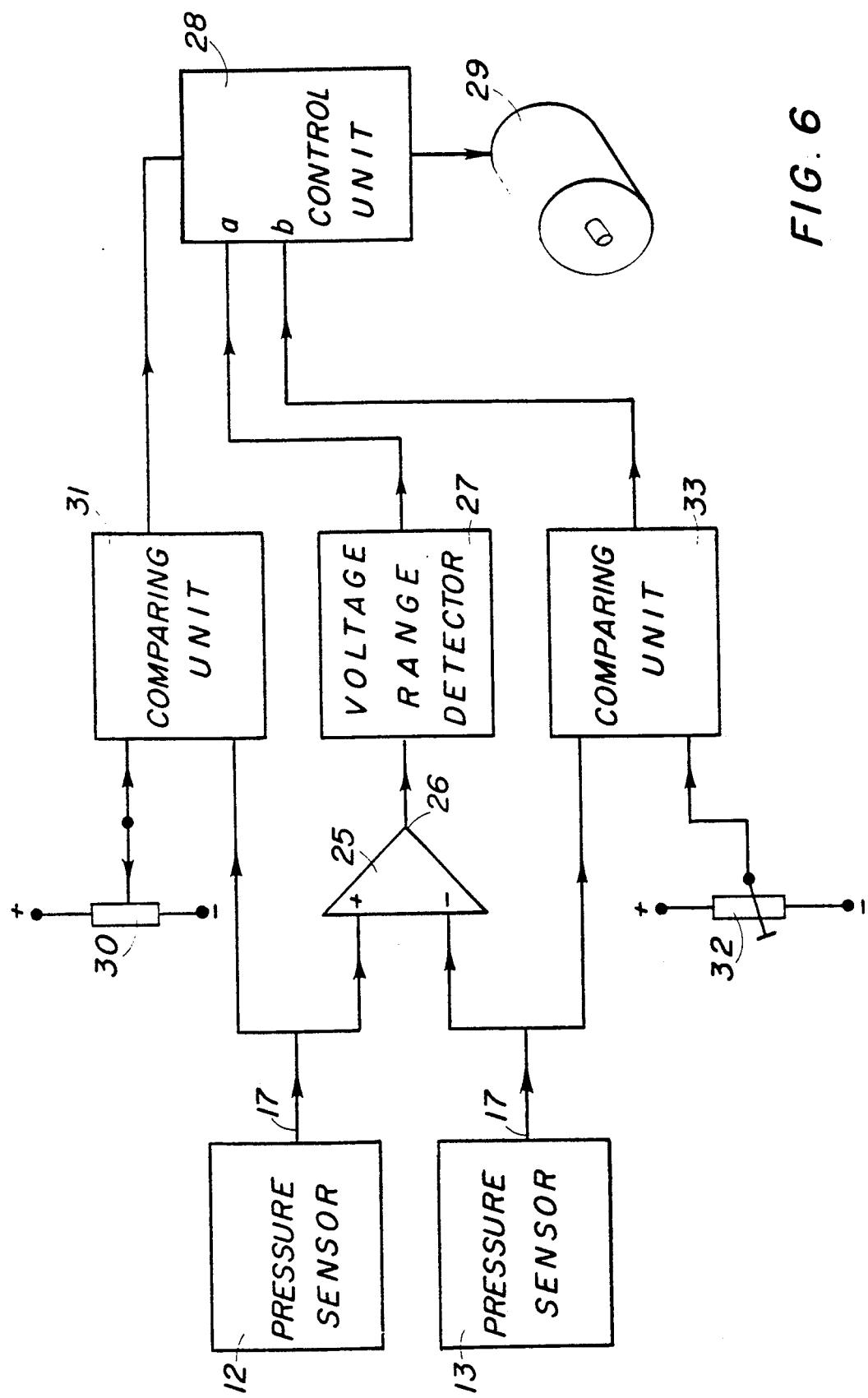

PRESSURE MEASUREMENT DEVICE FOR FLUIDS FLOWING IN LINES

FIELD AND BACKGROUND OF THE INVENTION

The invention generally concerns a pressure measurement device for fluids flowing in lines and more particularly concerns a pressure measurement device for fluids flowing in flexible tubing lines of pressure-controlled roller pumps such as peristaltic pumps for use in arthroscopy and urethroscopy.

A device of this type is known previously from DE 3,338,758. The pressure sensor used according to this reference can be a Stethem element, which is provided with a rigid pressure dome with two connections for a flexible tubing line and with a membrane sealing off the pressure dome. The rigid pressure dome with its membrane is pressed against a surface pressure sensor by means of a union nut.

The pressure sensor is introduced on the pressure surface lying opposite the membrane. Semiconductor sensors or wire strain gauges may be used as pressure sensors.

The transfer of fluid pressure via a sterile filter from a sterile flexible tubing setup to a nonsterile pressure sensor by means of an air column is also known. In addition, sterile disposable pressure sensors or resterilizable pressure sensors may be used, through which the fluid flow passes.

As the pressure built up in the body cavity is determined by the pressure sensor and the rpm of the roller pump is controlled, only a limiting device for a maximum pressure value is provided on the inlet side.

It is a disadvantage in conventional pressure measurement devices that the pressure control of the pump fails as soon as the pressure sensor or its evaluating electronic unit displays a first error. Such an error can be, for example, that the pressure sensor indicates a systemic pressure that is too low, although the actual system pressure is considerably higher and thus is dangerous for the patient. With previously known pressure measurement devices there is provided a measurement of the actual pressure without providing a control system determining whether or not the actual measured pressure is also the correct systemic pressure.

When fluid under pressure is transferred through an air column, another error source may be present due to a possible lack of tightness between the sterile filter and the pressure sensor.

In order to configure conventional pressure measurement devices in a more reliable manner, a mechanical overpressure safety device may be inserted in the line. However, this requires additional sterility measures and has the further disadvantage of a possible gumming up of the overpressure safety valve, e.g., when sugar-containing solutions are used. In addition, in the case of an overpressure, the fluid flowing in the line escapes into the atmosphere, whereby a considerable contamination of the treatment site occurs when a patient is treated.

The use of an additional overpressure safety valve, the use of disposable pressure sensors, and the use of resterilizable pressure sensors usually involves an increased labor expenditure, so that use of these items is not economical.

SUMMARY AND OBJECT OF THE INVENTION

The invention takes on the task of creating a pressure measurement device of the type discussed in the introduction, which makes possible in a simple way an independent monitoring of the measured pressure simultaneously with the pressure measurement, without necessitating a high construction expenditure.

According to the invention, a pressure measurement device and system are provided including a flexible tubing line employed with pressure-controlled roller pumps such as peristaltic pumps for use in arthroscopy and in urethroscopy, the flexible tubing lines including a membrane is under the pressure exerted by the fluid inside the lines. A pressure sensor is provided for measuring the fluid pressure. The pressure sensor is connected to an evaluating electronic device. The pressure sensor monitors the pressure from the outside of the membrane. A second pressure sensor is provided for monitoring the measured values. The second pressure sensor is connected to the evaluating electronic unit and senses pressure from the outside of the membrane.

A monitoring of the measured value is carried out in addition to the measurement of the actual pressure by the use of a second pressure sensor connected to the evaluating electronic unit. This monitoring is fully independent of the pressure measurement itself. The second pressure sensor monitoring occurs at the same time and is carried out at the same phase as the first monitoring. The second pressure sensor is thus electrically connected with the first pressure sensor via the evaluating electronic unit, so that a potentially existing pressure difference between the determined pressures can immediately indicate an error, which leads to the immediate switching off of the pump. The use of a special overpressure safety valve is thus no longer necessary. With the pressure measurement device according to the invention, both a pressure measurement of the actual pressure in the line as well as a pressure monitoring will be conducted at the same time and with equal phase, and the possible error in the pressure measurement or a pressure that is inadmissibly high or low will be indicated as soon as it occurs.

According to a particularly preferred embodiment of the invention, a flexible tubing piece is provided with a flexible tubing cushion of two membranes arranged parallel to each other and at a distance from each other, whereby one pressure sensor is assigned to each membrane. In this way, pressure sensors which are independent of each other and at the same time are identical in time and phase, and are assigned to each membrane, both measure the actual pressure value and, also monitor the pressure value and regularly indicate a possible pressure difference in the evaluating electronic unit and based on this evaluation, the pump may be switched off. The invention thus has an essential basic structural form of a flexible tubing piece with an integrated flexible tubing cushion of two parallel membranes. These will be as thin as possible and highly elastic, whereby a thickness of approximately 0.5 mm is preferred, whereby the remaining parts of the flexible tube line will have a wall thickness of a minimum of 1.5 mm.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 6 is a circuit diagram of an evaluating electronic unit according to the invention.

DETAILED DESCRIPTION OF THE PREFERRED EMBODIMENT

Figure 1:
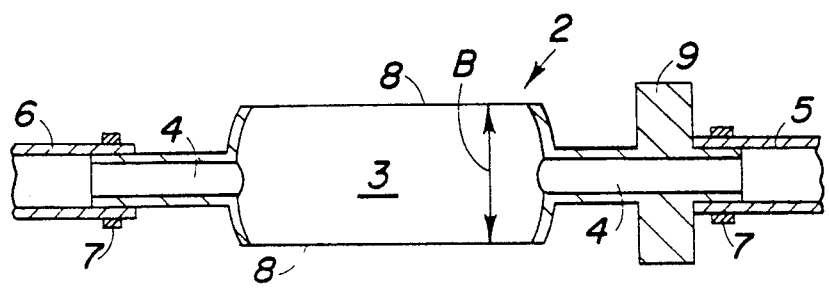
FIG. 1 is a longitudinal sectional view through a flexible tubing piece provided with a flexible tubing cushion according to a first embodiment of the invention.

Referring to the drawings in particular, the invention comprises a pressure measurement device 1 includes as an essential component a flexible tubing piece 2 with a flexible tubing cushion 3 and two flexible tubing ends 4. The flexible tubing ends 4 are rigidly inserted into additional flexible tubing lines 5, 6, and fastened by flexible tubing clamps 7. Flexible tubing cushion 3 consists of two membranes 8 made of thin, rubber-elastic material approximately 0.5 mm thick and arranged parallel to each other, whereas flexible tubing ends 4 have a wall thickness of at least 1.5 mm for reasons of stability. Membranes 8 are thus highly elastic. An essentially rectangular catch element 9 is formed at one flexible tubing end 4, which element is relatively rigid due to its size, as is shown in FIG. 1.

Figure 2:
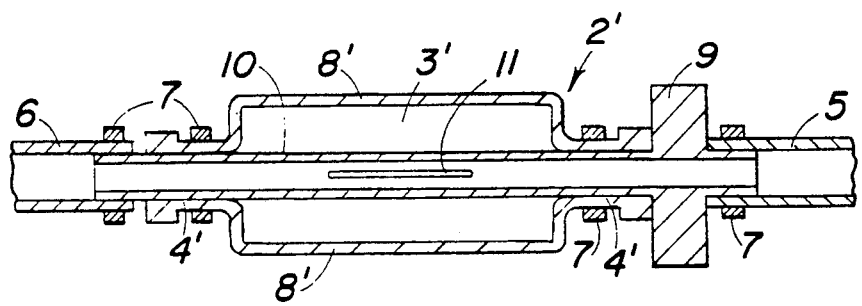
FIG. 2 is a longitudinal sectional view through a flexible tubing cushion inserted in the flexible tubing piece according to a second embodiment of the invention.

According to a second embodiment of the invention shown in FIG. 2, the flexible tubing piece 2' with its membranes 8' arranged lying parallel and opposite each other and flexible tubing ends 4' are essentially configured the same as flexible tubing piece 2 of the first form of embodiment, which is shown in FIG. 1. According to the second embodiment, a rigid inner tube 10, which is provided with longitudinal slots 11 in the region of membranes 8' for the passage of the fluid extends through the two flexible tubing ends 4'. The flexible tubing ends 4' are clamped with a flexible tubing clamp 7 on the inner tube, which in turn is connected by its ends with flexible tubing lines 5, 6 via additional flexible tubing clamp 7. The catch element 9' is formed in one piece with the inner tube 10.

A fluid flowing through flexible tubing piece 2,2' impacts upon the insides of membranes 8,8' in the region of the flexible tubing cushion 3,3' in such a way that a pressure is exercised outward, which equally affects the two membranes 8,8'. As a consequence of the relatively thin and thus highly elastic membranes 8,8', the bulging out of membranes 8,8', which is caused by the different fluid pressures, can be used for the purpose of measuring the pressure within flexible tubing piece 2,2' independent of each other at two different places at the same time and in the same phase by means of pressure sensors 12, 13 assigned to membranes 8,8'. Thus a pressure measurement can be used to determine the actual pressure, whereas the second pressure measurement is used for monitoring the pressure.

Figure 3:
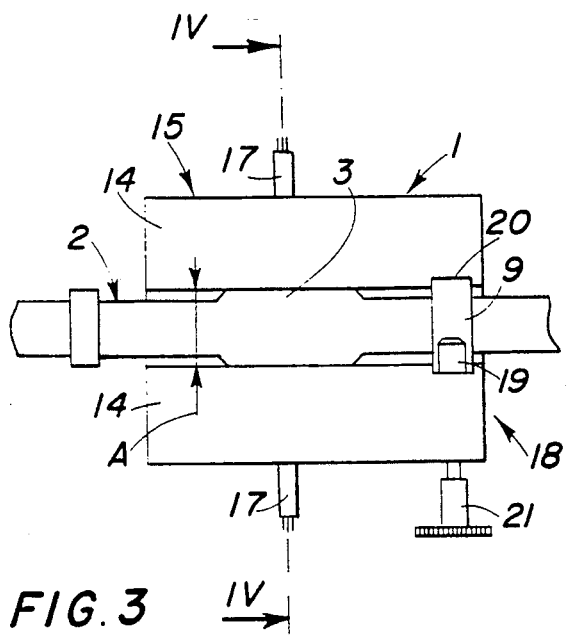
FIG. 3 is a top view of a pressure measurement device according to the invention.
Figure 4:
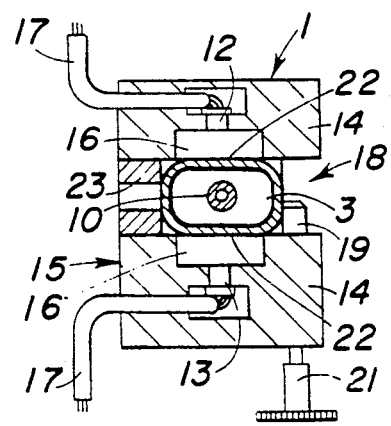
FIG. 4 is a cross-sectional view through the pressure measurement device according to line IV—IV in FIG. 3.

The pressure measurement device 1 shown in more detail in FIGS. 3 and 4 includes two supporting walls 14 arranged parallel to each other and separated by a separating piece 23 on the bottom for taking up flexible tubing piece 2,2' with its flexible tubing cushion 3,3'. The distance A between supporting walls 14 corresponds precisely to width B of the flexible tubing cushion 3,3' in the unloaded state.

Recesses 16 lying opposite each other are provided on the inside surfaces of the two supporting walls 14 that form a holding device 15, and the surface dimensions of the recesses are smaller than the surface dimensions of membranes 8,8'. Pressure sensors 12, 13 are inserted into the outside wall surfaces of recesses 16 and these sensors are joined with leads 17, which are guided to an evaluating electronic unit shown in FIG. 6. Recesses 16 are sealed by thin metal membranes 22 and are filled completely with compressed oil. As FIGS. 3 and 4 show, the flexible tubing piece 2,2' with its flexible tubing cushion 3,3' is found exactly between the two supporting walls 14 of holding device 15, whereby the flexible tubing cushions 3,3' for pressure transfer lie precisely on the thin metal membranes 22. Compressed oil columns, which serve for the transfer of pressure fluctuations from membranes 8,8', which cover recesses 16, to pressure sensors 12, 13 are formed in recesses 16.

To secure the position of flexible tubing cushion 3 within measurement holding device 15 such that rubber membranes 8,8' are flush with metal membranes 22 and cover the latter, a catch device 18 is provided, which is formed from the catch element 9 of flexible tubing piece 2 and a catch projection 19, which visibly secures the catch element 9 introduced into a guide 20 within supporting walls 14 against shifting. The distance between catch element 9 and the central axis of the flexible tubing cushion 3 is thus selected such that the latter precisely covers the metal membranes 22 with its membrane 8 in the locked position of catch element 9. Catch projection 19 is acted on by a spring-loaded handle 21.

Figure 5:
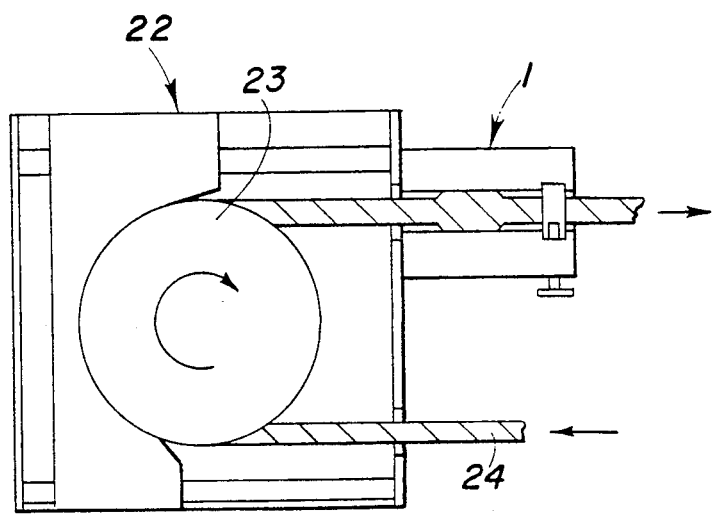
FIG. 5 is a top view of a roller pump with the pressure measurement device provided therein.

As is shown in FIG. 5, the pressure measurement device 1 is connected to a roller pump generally designated 22 in such a way that pressure measurement device 1 is arranged on the output side of a flexible tubing 24 placed around roller 23, whereby flexible tubing piece 2,2' may be an integral component of flexible tubing 24 or may be an independent component. FIG. 5 further shows that the user is forced to precisely clamp the flexible tubing cushion 3,3' within the two supporting walls 14 by means of catch device 18 at the same time that the pump flexible tubing 24 is fastened.

FIG. 6 shows schematically the circuit diagram of the evaluating electronic unit for pressure measurement device 1. Here, the two pressure sensors 12, 13, which are provided with their own amplifiers, are joined to a differential amplifier 25, at whose output 26 any pressure difference appears which may exist between the pressure values measured by means of pressure sensors 12, 13. This pressure difference is fed into a voltage range detector 27, which determines whether the pressure difference is within an allowed region or not. The output value of the voltage range detector 27 is passed to an emergency stop input a of the control electronic unit 28 of pump motor 29. A theoretical value-actual value comparing unit 33 (comparator) is also provided in the evaluating electronic unit for the preselected systemic pressure. This comparator is connected to a theoretical-value transmitter 30 and with one pressure sensor 12. The output value is also provided to the control electronic unit 28 for pump motor 29 in order to effect the pressure control of peristaltic pump or roller pump 22. Finally, an adjusting potentiometer 32 is provided in the evaluating electronic unit for the overpressure disconnection, and this is connected to an actual value-maximum value comparator 33, whose other input is connected with the second pressure sensor 13. The output of the actual value-maximum value comparator 33 is connected to the second emergency stop input b of control electronic unit 28 of motor 29. Pressure measurement device 1 operates in conjunction with the control electronic unit according to FIG. 6 in such a way that on the one hand one of the pressure sensors 12 supplies its pressure value directly via the theoretical value-actual value comparator 31 to the control electronic unit 28 of motor 29 of the roller pump 22 in order to control the latter as a function of the systemic pressure measured by means of pressure sensor 12 and that is selected beforehand by theoretical-value transmitter 30. The second pressure sensor 13 provides its pressure value directly to actual value-maximum value comparator 33, which is connected with adjusting potentiometer 32 for overpressure disconnection. The second pressure sensor 13 thus serves for pressure monitoring and effects a disconnection of the motor 29 of roller pump 22 in the case of a pressure exceeding the maximum pressure.

In addition, the pressure values of both pressure sensors 12, 13 are drawn on for conducting a measurement of difference in pressure by means of differential amplifier 25. As long as the determined pressure difference between the two pressure sensors 12, 13 exceeds the permitted range, which is monitored by the voltage range detector 27, motor 29 of roller pump 22 is disconnected by means of the associated control electronic unit 28.

The use of two pressure sensors 12, 13, which measure independently of one another and which are drawn on for the evaluation in three different pressure regions, is an essential element of the described pressure measurement device.

The other essential element and the core of the pressure measurement device, however, is flexible tubing cushion 3,3' with its two membranes 8,8', which are formed as highly elastic thin rubber membrane surfaces and which lie on metal membranes 22 of recesses 16 in order to transfer pressure changes to pressure sensors 12, 13 by means of compressed oil columns, which make possible a contactless transfer of pressure fluctuations from membranes 8,8' to pressure sensors 12, 13. Since flexible tubing pieces 2,2' may be produced as disposable products, and the remaining structural elements of pressure measurement device 1 need not be sterilized, pressure measurement device 1 is extremely simple in its handling and inexpensive in its manufacture.

While specific embodiments of the invention have been shown and described in detail to illustrate the application of the principals of the invention, it will be understood that the invention may be embodied otherwise without departing from such principals.

What is claimed is:

1. A pressure measurement system for fluids flowing in tubing lines of a pressure-controlled roller pump for use in arthroscopy and urethroscopy, comprising: a tubing line formed with a cushion element supporting first and second thin-walled membrane elements said membrane elements being substantially planar and substantially parallel, spaced a predetermined distance defining first and second tubing surfaces, said thin-walled membrane elements being under pressure exerted by fluid at a pressure level prevalent inside the tubing; first pressure sensor means, including a first pressure sensor element in contact with one of said surfaces, for monitoring the outside of said membrane fluid pressure of said fluid within said membrane; second pressure sensor means, including a second pressure sensor element in contact with one of said surfaces, for monitoring the outside of said membrane to measure pressure of said fluid within said membrane; a support arrangement including a first support wall and a second support wall defining a space for receiving said thin-walled membrane elements, said first support wall supporting said first pressure sensor means with said first pressure sensor element being positioned for contact with one of said surfaces, said second support wall supporting said second pressure sensor means positioning said second pressure sensor element in contact with one of said surfaces and, evaluating electronic means connected to each of said first sensor means and said second sensor means for monitoring measured values of said first sensor means and said second sensor means.

2. A pressure measurement system according to claim 1, wherein said first pressure sensor means and said second pressure sensor means are positioned for contact with the surface of said membrane positioned symmetrically with respect to said membrane.

3. A pressure measurement system according to claim 1, wherein said supporting walls include recesses, said first and second pressure sensor means being positioned opposite to each other in communication with said recesses, said recesses being filled with compressed oil and being covered by the first pressure sensor element and second pressure sensor element, each provided in the form of a metal membrane wherein force applied to the said metal membrane is transmitted through said oil to a corresponding sensor, said recesses being positioned such that such metal membranes are in contact with a central portion of said thin-walled membrane elements, each of said first pressure sensor means and said second pressure sensor means being connected to a different one of said two membranes.

4. A pressure measurement device according to claim 3, further comprising a catch device positioned in said holding device for positioning the flexible tubing piece with respect to said holding device.

5. A pressure measurement device according to claim 4, wherein said catch device includes a catch element connected to the flexible tubing piece associated with the flexible tubing cushion and two leads for maintaining said catch element between said supporting walls, said catch element including a catch projection for securing said catch element in said holding device.

6. A pressure measurement system according to claim 1, further comprising holding means for holding and supporting said thin-walled membrane elements first and second supporting walls defining recesses, said recesses being sealed by metal membranes and filled with compresses oil, said metal membranes being arranged facing a central recess, said flexible tubing cushion membranes being formed of rubber and being positioned within said recess.

7. A pressure measurement system according to claim 6, wherein said flexible tubing cushion includes an inner tube with an outlet opening, opening into an interior region of the flexible tubing cushion, said inner tube having ends connected with flexible tubing ends of a flexible tubing piece.

8. A pressure measurement system according to claim 1, wherein said evaluating electronic means includes a comparitor for comparing the pressure signal of one of said first sensor means and said second sensor means with one of a maximum pressure value and a preselected pressure value.

9. A pressure measurement system for fluids flowing in tubing lines of a pressure-controlled roller pump for use in arthroscopy and urethroscopy, comprising: a tubing line formed of a first thin-walled membrane element and a second thin-walled membrane element, said first thin-walled membrane element being connected to said second thin-walled membrane element by a tubing cushion arrangement and positioned spaced apart a predetermined distance, said first and second thin-walled membrane elements being connected sealingly to be under pressure exerted by fluid at a pressure level prevalent inside the tubing; holding means for holding and supporting said thin-walled membrane elements including first and second supporting walls spaced said predetermined distance apart such that said thin-walled membrane elements are in contact with said first and second supporting walls, said first and second supporting walls defining recesses, the said recesses being sealed by sealing membranes and filled with fluid, said sealing membranes being arranged facing said thin-walled membrane elements such that pressure exerted by fluid inside said tubing line exerts pressure on said sealing membranes through said thin-walled membrane elements and is transmitted through said fluid in said recess; a first pressure sensor means including a sensor surface in communication with one of said recesses for monitoring pressure in said tubing through said thin-walled membrane, said sealing membrane and said fluid in said recess; second pressure sensor means including a sensor element in communication with another of said recesses for sensing pressure in said tubing through said thin-walled membrane element, said sealing membrane and said fluid in said another of said recesses; and, evaluating electronic means connected to each of said first sensor means and said second sensor means for monitoring measured values of said first sensor means and said second sensor means.

10. A pressure measurement system for fluids flowing in tubing lines of a pressure-controlled roller pump comprising: a tubing line formed with a cushion element supporting first and second thin-walled membrane elements said membrane elements being substantially planar and substantially parallel, spaced a predetermined distance defining first and second tubing surfaces, said thin-walled membrane elements being under pressure exerted by fluid at a pressure level prevalent inside the tubing; first pressure sensor means for monitoring the outside of said membrane to measure fluid pressure of said fluid within said membrane; second pressure sensor means for monitoring the outside of said membrane to measure pressure of said fluid within said membrane; a support arrangement including a first support wall and a second support wall defining a space of said predetermined distance for receiving said membrane elements, said first support wall supporting said first pressure sensor means for contact with one of said surfaces, said second support wall supporting said second pressure sensor means in contact with one of said surfaces and, evaluating electronic means connected to each of said first sensor means and said second sensor means for monitoring measured values of said first sensor means and said second sensor means.

11. A pressure measurement system according to claim 10, wherein said evaluating electronic means includes a differential amplifier providing an output of a pressure difference between pressure signals of said first sensor means and said second sensor means.

* * * * *